United States Patent [19]

McCulloch et al.

[11] Patent Number: 5,031,126
[45] Date of Patent: Jul. 9, 1991

[54] CONSTANT POWER THERMAL SENSOR

[75] Inventors: Reginald W. McCulloch, Concord; Omar Garcia, Oak Ridge, both of Tenn.

[73] Assignee: Delta M Corporation, Oak Ridge, Tenn.

[21] Appl. No.: 496,067

[22] Filed: Mar. 16, 1990

Related U.S. Application Data

[63] Continuation of Ser. No. 213,319, Jun. 30, 1988, abandoned.

[51] Int. Cl.⁵ .............................................. G01K 7/00
[52] U.S. Cl. .............................. 364/557; 364/571.03; 340/622; 374/44; 374/183; 73/295
[58] Field of Search ............. 364/557, 571.01, 571.02, 364/571.03, 571.04; 73/295; 340/622; 374/3, 10, 43, 44, 54, 172, 183, 184, 185

[56] References Cited

U.S. PATENT DOCUMENTS

| | | | |
|---|---|---|---|
| 3,302,458 | 2/1967 | Scadron | 73/295 |
| 3,479,875 | 11/1969 | Riddell | 73/295 |
| 3,678,749 | 7/1972 | Harper | 73/304 |
| 4,102,199 | 7/1978 | Tsipouras | 364/557 |
| 4,209,837 | 6/1980 | Brown | 364/557 |
| 4,326,199 | 4/1982 | Tarpley et al. | 340/622 |
| 4,479,190 | 10/1984 | Takai et al. | 364/571.02 |
| 4,513,617 | 4/1985 | Hayes | 73/313 |
| 4,588,308 | 5/1986 | Saito | 364/557 |
| 4,590,797 | 5/1986 | Beaubatie et al. | 73/295 |
| 4,602,871 | 7/1986 | Hanaoka | 364/571.03 |
| 4,609,292 | 9/1986 | Asano et al. | 364/571.03 |
| 4,713,783 | 12/1987 | Fletcher | 364/557 |
| 4,771,393 | 9/1988 | Ishida et al. | 364/557 |

FOREIGN PATENT DOCUMENTS 0089203 9/1983 European Pat. Off. .
0142990 5/1985 European Pat. Off. .

Primary Examiner—Parshotam S. Lall
Assistant Examiner—Brian M. Mattson
Attorney, Agent, or Firm—Luedeka, Hodges, Neeley & Graham

[57] ABSTRACT

A constant power thermal property sensor compensates for changes in the temperature of the medium into which the sensor is disposed. The sensor has two side-by-side probes mounted in the medium with resistances that vary with temperature. A constant power source produces a current through the first probe and a current source applies a current to the second probe at a fixed ratio of the current in the first probe. The voltages across the probes are monitored and compared, and a signal is produced which is divided by current through the first probe. The resulting signal is representative of the heat transfer between the probes and the medium. The signal does not appreciably vary with changes in the temperature of the medium, and the medium may be a liquid, a gas, a liquid flow, a gas flow, or a combination of media. In this construction, two principal applications for the sensor are liquid level detectors and flow monitors.

10 Claims, 3 Drawing Sheets

CONSTANT POWER THERMAL SENSOR

This is a continuation of Ser. No. 07/213,319, filed June 30, 1988 now abandoned.

FIELD

The present invention relates to thermal property sensors and particularly relates to those sensors that compensate for changes in the temperature of the medium surrounding the sensor. The present invention also relates to liquid level sensors and particularly those sensors that compensate for changes in the temperature of the liquid.

BACKGROUND OF THE INVENTION

Thermal property sensors of the type described herein have a wide range of applications (e.g. detectors in gas-liquid chromatographs (GLC), flow monitors or liquid level detectors), and the basic concepts of their operation are well-known in prior art. A resistive element is heated and the resistance of the element is monitored to determine changed heat transfer conditions at the element. For example, if the medium surrounding the element changes from a gas to a liquid and becomes a better heat sink, much of the heat will be conducted away from the element, and the temperature of the element will decrease. This leads to a decrease in the resistance of the element which may be detected as an increase in the current through or a decrease in the voltage across the element or both.

Changes in the thermal properties of the medium such as thermal conductivity changes (e.g. a change in the composition of a GLC sample or a change in the level of a liquid) may be sensed by monitoring the changes in the current through and/or the voltage across the element. This works well in systems where the temperature of the medium remains constant.

Changes in the temperature of the medium will cause the temperature of the element to change as well. For example, a decrease in ambient temperature of the medium will decrease the resistance of the element and, as a consequence, the current will decrease or the voltage will increase. This change in ambient temperature may be misinterpreted as an increase in the thermal conductivity of the medium (i.e. the presence of a component in a GLC sample or an increase in the level of a liquid).

There are a number of attempts in the prior art to solve this problem. In gas-liquid chromatography, the carrier gas stream is apportioned into two paths prior to insertion of the sample, and a temperature reference is obtained from the second stream for providing temperature compensation. This ability to compensate for variations in temperature doubles the amount of gas needed for the chromatogram.

When measuring the level of a liquid, the prior art has resorted to the use of either a plurality of detectors or a temperature monitor in combination with a computer to compensate for the changes (such as is disclosed in U.S. Pat. No. 4,590,797, issued May 27, 1986 to Beaubatie, et al.). Others have assumed that there is no significant change in the temperature (such as is disclosed in U.S. Pat. No. 3,302,458, issued Feb. 7, 1967 to Scadron).

SUMMARY OF THE INVENTION

The present invention provides a constant indication of thermal conductivity property changes in a medium and minimizes the effects of changes in the ambient temperature of the medium. In accordance with the present invention, a constant power thermal property sensor provides for two probes with resistances that vary with temperature and are mounted side-by-side in a medium in which the thermal properties along the probes change over time through a known range. For example, if the probes were mounted in a tank, a changing liquid level in the tank would constitute changing thermal properties along the probes. A constant power source produces a current through the first probe and a current source applies a current to the second probe at a fixed ratio of the current in the first probe. The voltages across the probes are monitored and compared, and a signal is produced which is divided by a signal representative of the current through the second probe. The resulting signal is representative of the thermal property changes in the medium, such as changes in thermal conductivity. The signal does not appreciably vary with changes in the temperature of the medium, and the medium may be a liquid, a gas, a liquid flow, a gas flow, or a combination of media.

In the preferred embodiment of the present invention, a current, $I_1$, is applied through the first probe, a reference probe, from a constant power source. The current through the reference probe is insufficient to cause significant self-heating. A current, $I_2 = kI_1$, is also applied through a second probe, a hot probe. That current is a fixed ratio, k, of the current through the reference probe, and it is sufficient to cause self-heating in the hot probe.

The resistances of the reference probe, $R_1$, and the hot probe, $R_2$, are given by:

$$R_1 = R_0(1 + \alpha \Delta t_a),$$

$$R_2 = R_0(1 + \alpha \Delta t_a + \alpha \Delta t_s),$$

where $R_0$ is the resistance of the probes at some initial temperature, $t_0$; $\alpha$ is the temperature coefficient of resistance of the probe material, $\Delta t_a$ is the difference between $t_0$ and the temperature of the medium, and $\Delta t_s$ is the difference between $t_a$ and the temperature of the hot probe. The temperature of the self-heated hot probe is affected by both the thermal properties, primarily thermal conductivity, of the medium and the power through the probe. Changes in ambient temperature of the medium will not appreciably change the thermal conductivity and other thermal properties of the medium, but it will change the temperature of the hot probe.

The resistance and temperature of the reference probe is also affected by changes in ambient temperature. As the ambient temperature changes, the resistance in and the current through the reference probe changes as power remains constant. The amount of current, $I_2$, through the hot probe is some fixed ratio of the current through the temperature probe. Therefore, assuming constant thermal medium properties, the current through the hot probe varies only with changes in ambient temperature. In addition, the voltage across the reference probe provides a measure of the ambient temperature of the medium.

The voltages across the reference probe, $V_1$, and the hot probe, $V_2$, are given by:

$$V_1 = I_1 R_1 \text{ and}$$

$$V_2 = kI_1R_2.$$

The voltage across the reference probe, $V_1$, is multiplied by the fixed ratio, k, and applied to a subtraction circuit. The voltage across the hot probe, $V_2$, is also applied to the subtraction circuit and a resulting voltage, $V_T$, is produced which is the difference between the two voltages as follows:

$$V_T = V_2 - kV_1 = kI_1R_0\alpha\Delta t_s$$

The resulting voltage ($V_T$) is applied to a divider circuit where it is divided by the current through the hot probe, $kI_1$, to give a signal which is representative of the change in temperature due to the change in thermal property, $\Delta t_s$:

$$V_T/kI_1 = R_0\alpha(\Delta t_s) = K\Delta t_s$$

where K is the product of $R_0$ and $\alpha$. The signal will vary with a change in temperature due to a change in thermal conductivity, such as a liquid level change. The signal will not appreciably change due to a change in ambient temperature of the medium.

The invention may be used wherever the continuous measurement of the thermal properties of a medium is desired. In addition, changes in the ambient temperature of the medium will not appreciably affect the accuracy of the measurement. The invention is especially applicable to liquid level measurements and to thermal conductivity measurements, such as the measurements performed in gas-liquid chromatographs.

BRIEF DESCRIPTION OF THE DRAWINGS

The present invention may be best understood by reference to the following detailed description of exemplary embodiments when considered in conjunction with the drawings in which.

DETAILED DESCRIPTION OF THE DRAWINGS

Figure 1:
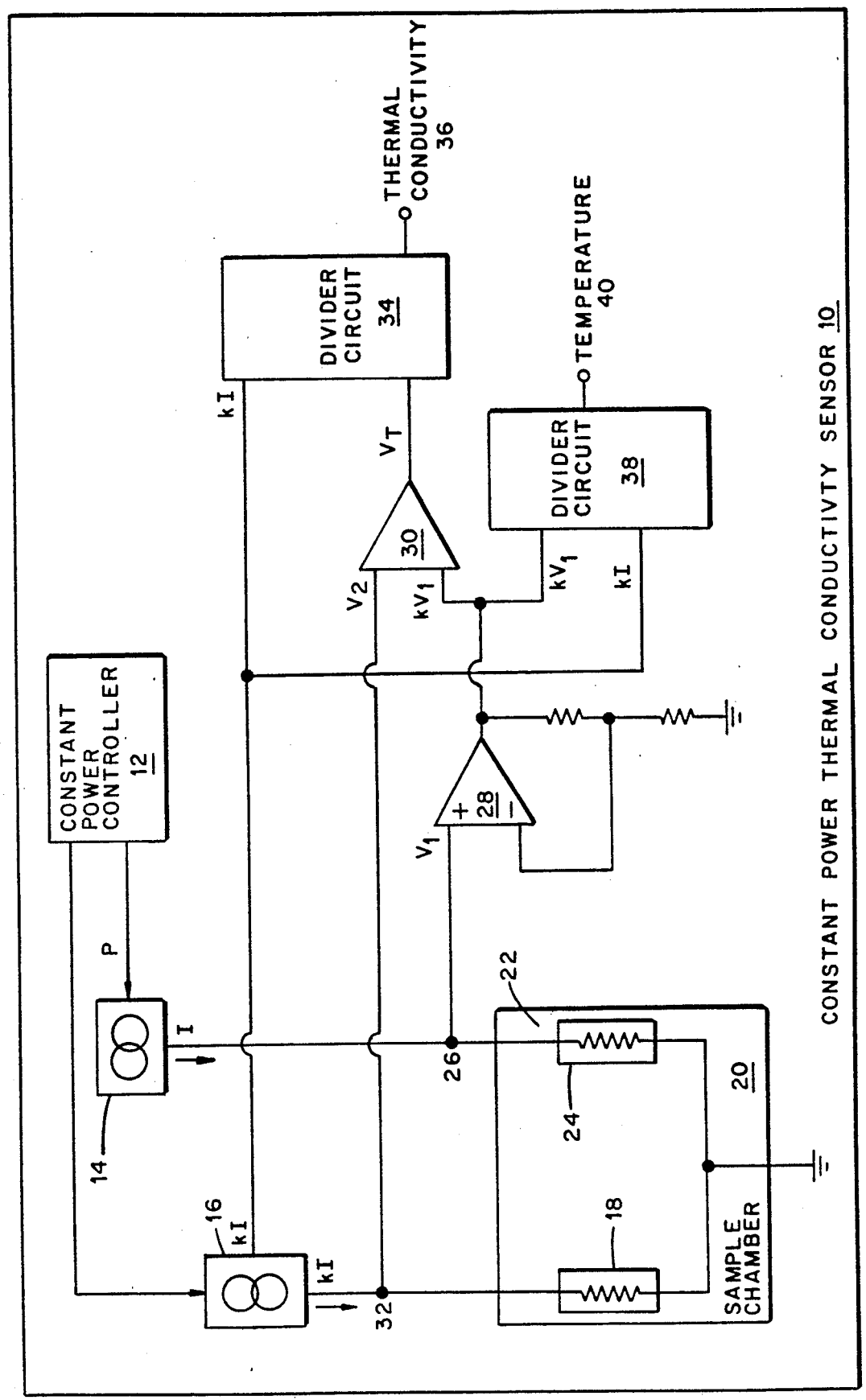
FIG. 1 is a schematic block diagram of a constant power thermal properties sensor.

Referring now to the drawings in which like reference characters designate like or corresponding parts throughout the several views, there is shown in FIG. 1 a constant power thermal properties sensor 10 embodying the present invention. The sensor 10 includes a constant power controller 12 which provides a constant source of power, P, to current source 14. Source 14 applies a current, $I_1$, to current source 16 which supplies a current, $kI_1$, that is a fixed multiple, k, of the current from source 14. The current, $kI_1$, from source 16 is applied to a hot probe 18 which is mounted in sample chamber 20. The current, $kI_1$, through the resistance, $R_2$, of hot probe 18 causes self-heating in probe 18. The self-heating is at least partially quenched by the medium 22 in sample chamber 20, and the medium 22 will have changing thermal properties within a known range. At a constant temperature in sample chamber 20, a change in the thermal properties of medium 22 will be seen as a change in the temperature hot probe 18. For example, when the thermal conductivity of the medium 22 increases, the temperature of probe 18 decreases as does the resistance, $R_2$. Since the current, $kI_1$, through probe 18 is constant, the voltage, $V_2$, across the probe 18 decreases. If the thermal conductivity of the medium 22 decreases, the effects on resistance, $R_2$, and voltage, $V_2$, will be reversed.

Changes in the ambient temperature of medium 22 will also cause a change in the quenching of the self-heating of the probe 18. A reference probe 24 is mounted side-by-side with hot probe 18 in sample chamber 20. Reference probe 24 is supplied with current, $I_1$, from current source 14. Current, $I_1$, is not sufficient to cause appreciable self-heating of probe 24 in medium 22. As the temperature of medium 22 in sample chamber 20 changes, the resistance, $R_1$, of reference probe 24 and the current, $I_1$, through $R_1$ changes. The change in $I_1$ is reflected in a proportional change in the current, $kI_1$, through the hot probe 18. For example, when the ambient temperature in medium 22 increases, the temperature of reference probe 24 increases as does the resistance, $R_1$. The increase in resistance, $R_1$, results in a decrease in current, $I_1$, through probe 24. Voltage, $V_1$, across probe 24 increases since power, P, is held constant by controller 12. The decrease in current, $I_1$, causes a decrease in current, $kI_1$, from current source 16 through hot probe 18. If the ambient temperature in medium 22 decreases, the effects on resistance, $R_1$, voltage, $V_1$, current, $I_1$, and current, $kI_1$, will be reversed.

The voltage, $V_1$, across reference probe 24 is measured at point 26 and applied to operational amplifier 28. Operational amplifier 28 amplifies the voltage, $V_1$, by the fixed ratio, k, of the hot probe current, $kI_1$, to the reference probe current, $I_1$. Operational amplifier 28 produces a multiplied voltage signal, $V_m = kV_1$, which is applied to instrumentation amplifier 30. Instrumentation amplifier 30 also receives the voltage, $V_2$, across hot probe 18 as measured at point 32.

The output voltage, $V_T$, of instrumentation amplifier 30 is the difference between the voltage, $V_2$, across hot probe 18 and the amplified voltage, $kV_1$, from operational amplifier 28. Output voltage, $V_T$, is applied to divider circuit 34 along with hot probe current, $kI_1$, from current source 16. The output signal, $K\Delta t_s$, from divider circuit 34 results from the division of voltage, $V_T$, by current, $kI_1$. The signal is applied to output 36. The output signal, $K\Delta t_s$, is proportional that portion of the temperature change of the hot probe 18 which reflects changes in the thermal properties (usually thermal conductivity) of the medium 22.

The effects on output signal, $K\Delta t_s$, of changes in the ambient temperature of the medium 22 are minimized first by providing a constant power controller 12 which minimizes the effects of changes in the ambient temperature on the self-heating of the hot probe 18. Any changes in the ambient temperature of the medium 20 are detected as changes in resistance, $R_1$, of the reference probe 24. The change in resistance, $R_1$, results in a change in the current, $I_1$, through the reference probe 24 and in the current $kI_1$, applied through the hot probe 18. Therefore, the output 36 is proportional to the thermal conductivity of the medium 22 and does not vary appreciably with changes in the ambient temperature of the medium 22.

The ambient temperature of the medium may be measured by applying the voltage signal, $kV_1$, from operational amplifier 28 and the hot current, $kI_1$, from current controller 16 to divider circuit 38. The output 40 from the divider circuit 38 is a signal, $K\Delta t_a$, that is representative of the ambient temperature of the medium 22.

Figure 2:
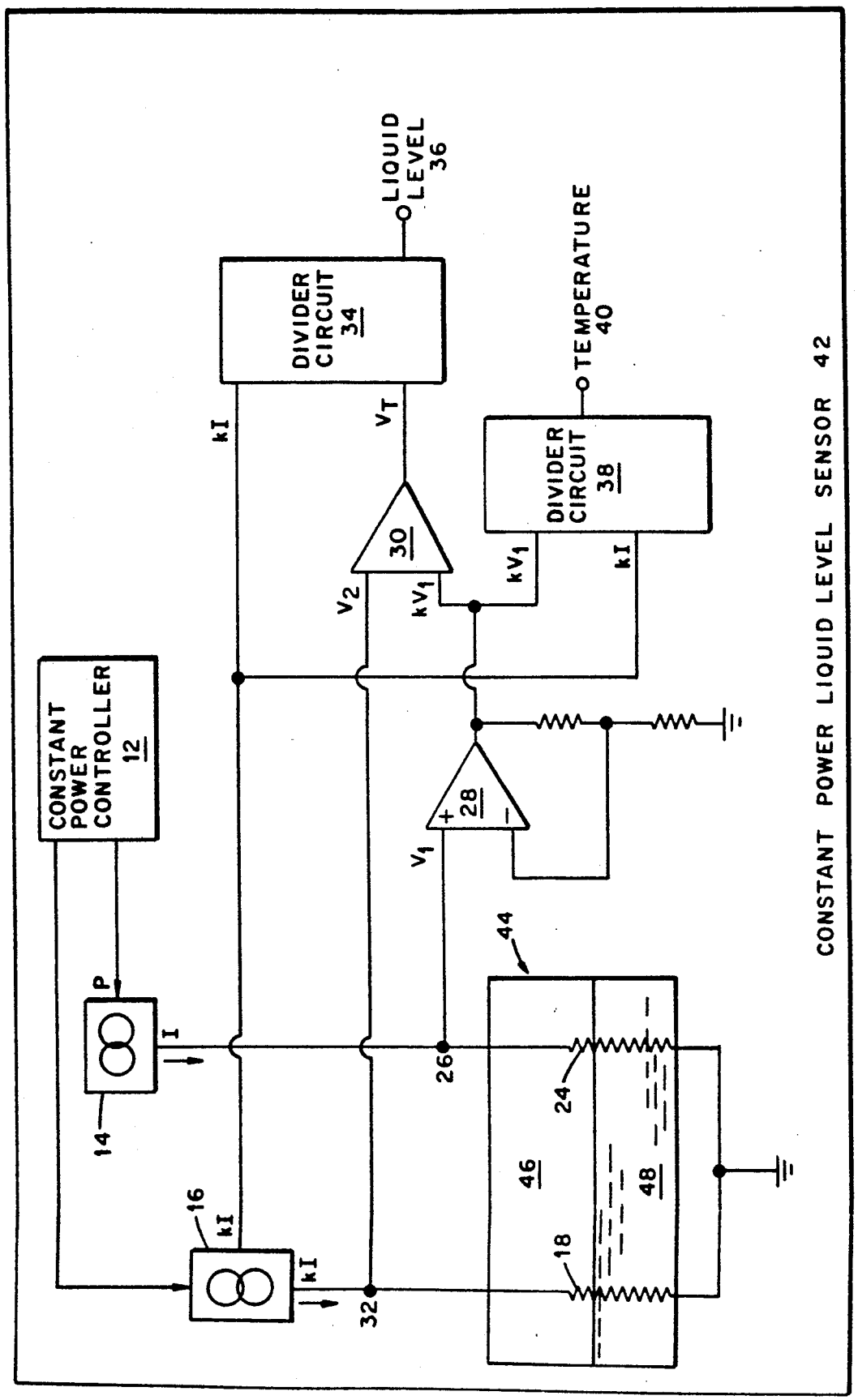
FIG. 2 is a schematic block diagram of a liquid level sensor that utilizes the concepts embodied in the present invention.

There is shown in FIG. 2 a constant power liquid level sensor 42 embodying the present invention. This embodiment of the invention may also be used to measure the relative levels of any immiscible components with differing thermal conductivities, such as water and gasoline, or air and sand. The liquid level sensor 42 is similar to the constant power thermal property sensor 10 except that the sample chamber 20 is a container 44, and the medium 22 is a liquid-gas mix where the gas 46 has a thermal conductivity that is different from the liquid 48. The discussion that follows assumes that the liquid 48 has a higher thermal conductivity than the gas 46. A similar discussion may be applied to the case of a gas 46 with a higher thermal conductivity.

As the level of liquid 48 rises and falls, more or less of the hot probe 18 will be covered by the liquid 48. If the liquid has a high thermal conductivity, then the liquid covered portion of the probe 18 will be quenched and the self-heated temperature of the covered part of the probe 18 will decrease. This decrease in the temperature of the hot probe 18 will cause its resistance, $R_2$, to decrease Since the current $kI_1$, through the probe 18 is held constant at a constant ambient temperature, only the voltage, $V_2$, across the probe 18 will be affected by the quenching; the voltage, $V_2$, will fall in proportion to the drop in resistance, $R_2$, in the probe 18.

The output signal, $K\Delta t_s$, will be proportional to the amount of hot probe 18 exposed, or covered, by liquid 48 in container 44. The signal, $K\Delta t_s$, will not be appreciably affected by changes in the ambient temperature of the liquid 48 or gas 46 in container 44. Reference probe 24 and the associated circuitry provide ambient temperature compensation in the same manner as in the constant power thermal property sensor 10. In addition, the temperature of the medium may be monitored in a manner similar to that discussed previously in relationship to the constant power thermal property sensor 10.

Figure 3:
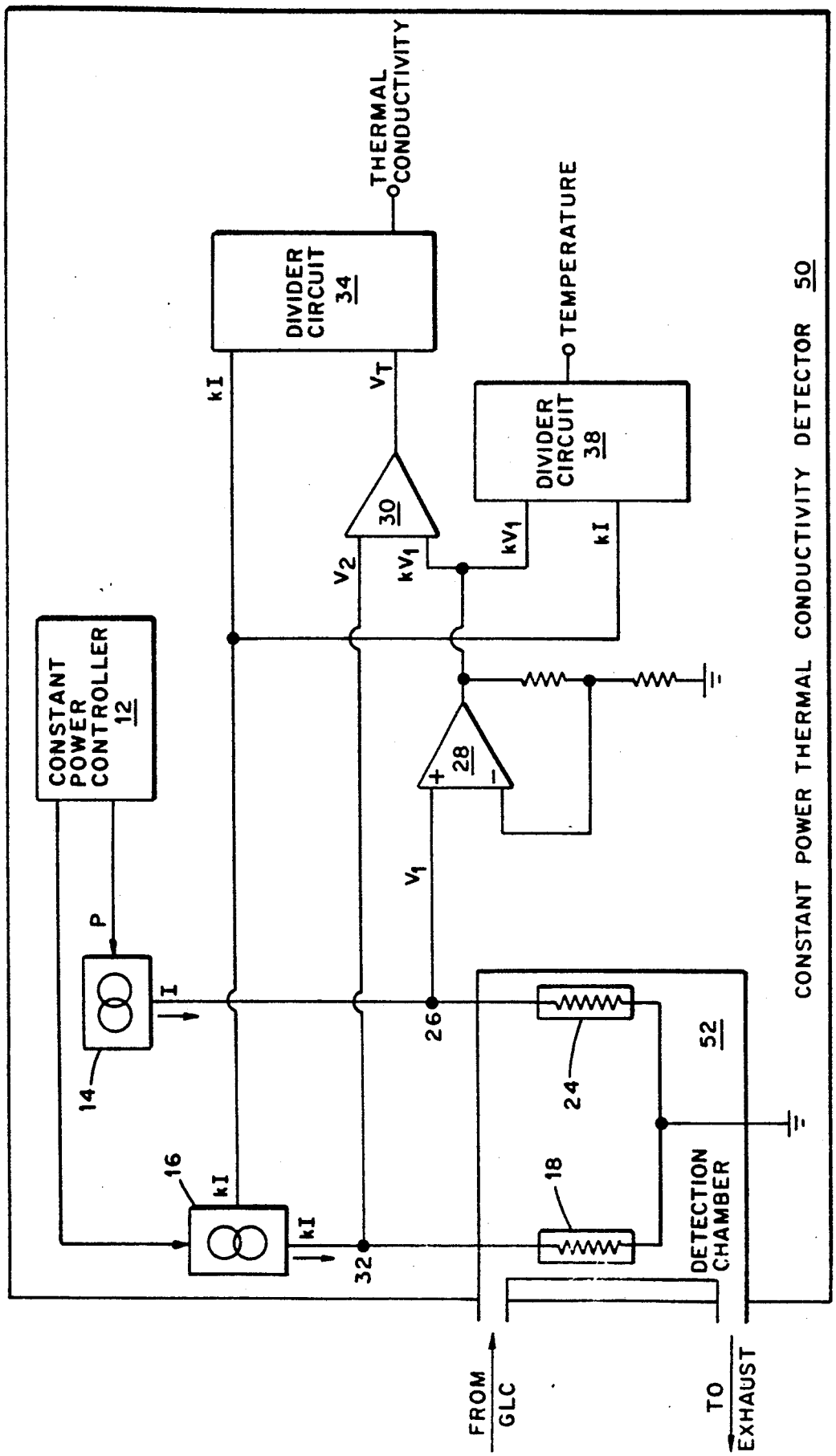
FIG. 3 is a schematic block diagram of a thermal conductivity detector for a gas-liquid chromatograph that utilizes the concepts embodied in the present invention.

Shown in FIG. 3 is a constant power thermal conductivity detector 50 embodying one form of the present invention for use with a gas-liquid chromatograph. The detector 50 is similar to the constant power thermal property sensor 10 except that the sample chamber 22 is a detection chamber 52. The medium 22 is a flowing gas solution that has passed through a GLC column.

The primary component of medium 22 is a carrier gas, usually helium or argon, with a high thermal conductivity. As gaseous organic components of the sample come off the column and into detection chamber 52, they pass over the self-heated hot probe 18. The organic components have thermal conductivities that are substantially below that of the carrier gas, and as they pass over probe 18, less heat is conducted away. This causes the self-heated temperature of probe 18 to increase. The resistance, $R_2$, of probe 18 increases and, since the current, $kI_1$, is constant at a constant ambient temperature, voltage, $V_2$, decreases.

The output signal, $K\Delta t_s$, will be proportional to the amount of organic compound in the carrier gas. A large amount of organic compound will cause a large change in the output signal, $K\Delta t_s$. A small amount will cause a smaller change. The signal, $K\Delta t_s$, will not be appreciably affected by changes in the ambient temperature of the medium 22. Reference probe 24 and associated circuitry provide ambient temperature compensation in the same manner as in the constant thermal property sensor 10.

The temperature of the medium may be monitored in a manner similar to that discussed previously in relationship to the constant power thermal property sensor 10.

From the foregoing discussion, it will be appreciated that the present invention provides a thermal properties sensor that supplies a continuous measure of the change in thermal properties of a medium and may be used in a wide variety of applications. In addition, the measurement will not be appreciably affected by changes in the ambient temperature of the medium. This invention avoids many of the problems associated with prior art thermal property sensors.

What is claimed is:

1. A sensor for determining thermal properties of a medium surrounding the sensor while compensating for changes in temperature of the medium, the sensor comprising:
   a first probe for being mounted in the medium, said first probe having a resistance which varies with temperature;
   a second probe for being mounted in the medium, said second probe having a resistance which varies with temperature;
   means for mounting said first and second probes side-by-side in the medium;
   a constant power source connected for producing a current through and a voltage across at said first probe;
   a current source connected for applying a current through said second probe at a fixed multiple of the current in said first probe sufficient to cause self-heating of said second probe, and producing a voltage across said second probe;
   means connected for monitoring the voltages across said first and second probes; and
   means for comparing the voltage across said first and second probes to produce a signal representative of the thermal properties of the medium.

2. The sensor of claim 1, wherein said means for comparing the voltages across said first and second probes to produce a signal representative of the thermal conductivity of the medium comprises:
   means for multiplying the voltage across the first probe by said fixed multiple;
   means for producing a reference voltage signal that is proportional to the voltage across the first probe;
   means for comparing the voltage across the second probe and the reference voltage signal to produce a difference voltage signal; and
   means for dividing the difference voltage signal by a signal representative of the current through said second probe to produce a signal that is representative of the thermal properties of the medium.

3. The sensor of claim 1, wherein:
   the medium is a combination of liquid and gas, the liquid having a level to be measured; and
   the signal representative of the thermal properties of the medium is a signal representative of the level of the liquid.

4. The sensor of claim 1, further comprising means for producing a signal representative of the temperature of the medium.

5. The sensor of claim 4, wherein said means for producing a signal representative of the ambient temperature of the medium comprises:

means for multiplying the voltage across the first probe by said fixed multiple to produce a voltage signal that is proportional to the voltage across the first probe; and means for dividing the voltage signal that is proportional to the voltage across the first probe by a signal representative of the current through the second probe to produce a signal that is representative of the ambient temperature of the medium.

6. A sensor for determining thermal properties of a medium surrounding the sensor while compensating for changes in temperature of the medium, the sensor comprising:

a first probe for being mounted in the medium, said first probe having a resistance given by the equation:

$$R_1 = R_0(1 + \alpha \Delta t_a)$$

where $R_1$ equals said resistance of said first probe at an ambient temperature;

$R_0$ equals a resistance of said first probe at an initial temperature;

$\alpha$ equals a temperature coefficient of resistance of said first probe; and $\Delta t_a$ equals a difference between said initial temperature and said ambient temperature;

a second probe for being mounted in a medium, said second probe having a resistance given by the equation:

$$R_2 = R_0(1 + \alpha \Delta t_a + \alpha \Delta t_s)$$

where $R_2$ equals said resistance of said second probe at a self-heated temperature; and $\Delta t_s$ equals a difference between said ambient temperature and said self-heated temperature;

means for mounting said first and second probes side-by-side in the medium;

a constant power source connected for producing a current through and a voltage across said first probe, said voltage given by the equation:

$$V_1 = I_1 R_1$$

where $V_1$ equals the voltage across said first probe; and
$I_1$ equals the current through said first probe;

a current source connected for applying a current through said second probe at a fixed multiple of said current through said first probe sufficient to cause self-heating of said second probe, said current through said second probe given by the equation:

$$I_2 = kI_1, \text{ and}$$

where $I_2$ equals said current through said second probe; and $k$ equals said fixed multiple, and said current source producing a voltage across said second probe, said voltage given by the equation:

$$V_2 = I_2 R_2 = kI_1 R_2$$

where $V_2$ equals the voltage across said second probe;

means for multiplying said voltage across said first probe by said fixed multiple producing a multiplied voltage given by the equation:

$$V_m = kV_1$$

where $V_m$ equals said multiplied voltage;

means for subtracting said multiplied voltage from voltage across said second probe producing a resulting voltage given by the equation:

$$V_T = V_2 - kV_1 = kI_1 R_0 \alpha \Delta t_s$$

where $V_T$ equals said resulting voltage; and means for dividing said resulting voltage by said current of said first probe, said means producing a signal given by the equation:

$$V_T/I_2 = V_T/kI_1 = R_0 \alpha \Delta t_s,$$

whereby said signal is representative of the thermal properties of the medium.

7. The sensor of claim 6, further comprising:

means for multiplying said voltage across said first probe by said fixed multiple and producing a multiplied voltage signal that is proportional to the voltage across said first probe, said multiplied voltage given by the equation:

$$V_m = kV_1$$

where $V_m$ equals said multiplied voltage; and means for dividing said multiplied voltage signal by said current through said second probe and producing a signal given by the equation:

$$V_m/I_2 = kV_1/kI_1 = R_0 \alpha \Delta t_{a1},$$

whereby said signal is representative of said ambient temperature of the medium.

8. A sensor for determining thermal properties of a medium surrounding the sensor while compensating for changes in temperature of the medium, the sensor comprising:

a first probe for being mounted in the medium, said first probe, having a resistance which varies with temperature;

a second probe for being mounted in the medium, said second probe having a resistance which varies with temperature;

means for mounting said first and second probes side-by-side in the medium;

a constant power source connected for producing a constant power;

a first current source connected to said constant power source for producing a current through and a voltage across said first probe;

a second current source connected for applying a current through said second probe at a fixed multiple of the current in said first probe and producing a voltage across said second probe;

a multiplier circuit for receiving the voltage across said first probe and multiplying said voltage by said fixed multiple producing a multiplied voltage signal;

a subtraction circuit for subtracting said multiplied voltage signal from the voltage across said second probe producing a resulting voltage; and a divider circuit for dividing said resulting voltage by the current through said second probe and producing a signal that is representative of the thermal properties of the medium.

9. The sensor of claim 8, further comprising a divider circuit for dividing said multiplied voltage signal by the current through said second probe and producing a signal that is representative of the temperature of the medium.

10. A sensor for determining thermal properties of a medium surrounding the sensor while compensating for changes in temperature of the medium, the sensor comprising:

first and second probes each having a resistance which varies with temperature;

means for mounting said probes side-by-side in the medium;

a constant power source connected for producing a current through and a voltage across each of said probes while maintaining constant power in at least one of said probes, and producing more current through said second probe than through said first probe sufficient to cause self-heating of said second probe, while maintaining a fixed ratio between the respective currents through said probes;

means for monitoring the voltages across said probes; and means for comparing the voltages across said probes to produce a signal representative of the thermal properties of the medium.

* * * * *